(12) United States Patent
Flynn et al.

(10) Patent No.: US 9,757,221 B2
(45) Date of Patent: Sep. 12, 2017

(54) MEDICAL DEVICE AND METHOD OF MAKING THE SAME

(71) Applicant: Boston Scientific Scimed, Inc., Maple Grove, MN (US)

(72) Inventors: Kenneth M. Flynn, Woburn, MA (US); Peter J. Pereira, Mendon, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 319 days.

(21) Appl. No.: 14/478,721

(22) Filed: Sep. 5, 2014

(65) Prior Publication Data
US 2015/0080648 A1 Mar. 19, 2015

Related U.S. Application Data

(60) Provisional application No. 61/878,440, filed on Sep. 16, 2013.

(51) Int. Cl.
*A61F 2/04* (2013.01)
*A61F 2/00* (2006.01)
*B23K 26/00* (2014.01)

(52) U.S. Cl.
CPC .......... *A61F 2/0045* (2013.01); *A61F 2/0063* (2013.01); *B23K 26/0066* (2013.01); *A61F 2230/006* (2013.01); *A61F 2230/0069* (2013.01); *A61F 2240/001* (2013.01); *Y10T 29/49826* (2015.01)

(58) Field of Classification Search
CPC ........ A61F 2/00; A61F 2/0004; A61F 2/0031; A61F 2/0036; A61F 2/0045; A61F 2/0063; A61F 2002/0068; A61F 2230/0069; A61B 2017/00805
See application file for complete search history.

(56) References Cited

U.S. PATENT DOCUMENTS

| | | | |
|---|---|---|---|
| 4,854,316 A * | 8/1989 | Davis | A61F 2/0063 128/898 |
| 7,985,173 B2 | 7/2011 | Jacquetin | |
| 7,985,174 B2 | 7/2011 | Nicita | |
| 7,998,055 B2 | 8/2011 | Siegel et al. | |
| 8,057,382 B2 | 11/2011 | Thierfelder et al. | |
| 8,109,867 B2 | 2/2012 | Rosenblatt | |
| 8,262,557 B2 | 9/2012 | Chapman et al. | |
| 2002/0095181 A1 | 7/2002 | Beyar | |
| 2005/0101834 A1 | 5/2005 | Merade | |
| 2007/0065224 A1 * | 3/2007 | Shaw | A47K 7/03 401/201 |
| 2007/0142698 A1 * | 6/2007 | Bourne | A61F 2/0045 600/30 |
| 2007/0173864 A1 | 7/2007 | Chu | |
| 2007/0270890 A1 | 11/2007 | Miller | |
| 2008/0119863 A1 | 5/2008 | Mellier | |

(Continued)

FOREIGN PATENT DOCUMENTS

WO 2007/106897 A2 9/2007

*Primary Examiner* — Samuel Gilbert
*Assistant Examiner* — Thaddeus Cox
(74) *Attorney, Agent, or Firm* — Brake Hughes Bellermann LLP

(57) ABSTRACT

In an embodiment, a medical device is a bodily implant and includes an elongate member. The elongate member has an inner edge that defines an opening. At least a portion of the inner edge being treated.

19 Claims, 6 Drawing Sheets

(56) References Cited

U.S. PATENT DOCUMENTS

| | | |
|---|---|---|
| 2008/0146886 A1 | 6/2008 | Lucas |
| 2008/0221386 A1* | 9/2008 | Gellman .......... A61B 17/00234 600/37 |
| 2009/0082791 A1* | 3/2009 | Schroeder ............. A61F 2/0059 606/151 |
| 2009/0171143 A1 | 7/2009 | Chu et al. |
| 2009/0326573 A1 | 12/2009 | Miller |
| 2010/0056857 A1* | 3/2010 | Nordmeyer ........... A61F 2/0045 600/30 |
| 2010/0305394 A1* | 12/2010 | Rosenblatt ............ A61F 2/0063 600/30 |
| 2011/0082478 A1* | 4/2011 | Glick ............... A61B 17/06166 606/148 |
| 2012/0083807 A1 | 4/2012 | Mathisen et al. |
| 2012/0108894 A1 | 5/2012 | Young et al. |
| 2013/0006050 A1 | 1/2013 | Rane et al. |

* cited by examiner

MEDICAL DEVICE AND METHOD OF MAKING THE SAME

CROSS-REFERENCE TO RELATED APPLICATION

This application is a Nonprovisional of, and claims priority to, U.S. Patent Application No. 61/878,440, filed on Sep. 16, 2013, entitled "MEDICAL DEVICE AND METHOD OF MAKING THE SAME", which is incorporated by reference herein in its entirety.

BACKGROUND

Field

The present invention generally relates to medical devices, methods of making medical devices, and procedures for placing medical devices within a body of a patient.

Description of the Related Art

Pelvic organ prolapse is an abnormal descent or herniation of the pelvic organs. A prolapse may occur when muscles and tissues in the pelvic region become weak and can no longer hold the pelvic organs in place correctly.

Treatment for symptoms of the pelvic organ prolapse can include changes in diet, weight control, and lifestyle. Treatment may also include surgery, medication, and use of grafts to support the pelvic organs.

Sacrocolpopexy is one such surgical technique that may be used to repair pelvic organ prolapse. This can be performed using an open abdominal technique or with the use of minimally invasive surgery, such as laparoscopy or robotic-assisted surgery. The technique can include suspension of the apical portion of vagina (or sometimes the vaginal cuff after hysterectomy) using an implant. In some cases, the technique may attempt to recreate the natural anatomic support of the vagina.

In some cases, a Y-shaped implant may be used to treat vaginal vault prolapse during the sacrocolpopexy procedure. The Y-shaped implant aids vaginal cuff suspension to the sacrum and may provide long-term support. The procedure can be minimally invasive (laparoscopic sacral colpopexy) or traditional (open sacral colpopexy). Also, in some cases, different anatomical locations inside a patient's body for example, vagina, uterus, and sacrum may be involved in repair of the pelvic organ prolapse. For example, at least a portion of the implant may be attached to an anterior vaginal wall, another portion of the implant may be attached to a posterior vaginal wall, and another portion of the implant may be attached to the sacrum or to tissue proximate the sacrum.

Thus, in light of the above, there is a need for an improved implant efficiently and effectively implanted within the body to provide support to pelvic organs such as the vagina.

SUMMARY

In an embodiment, a medical device is a bodily implant and includes an elongate member. The elongate member has an inner edge that defines an opening. At least a portion of the inner edge being treated.

In another embodiment, a method of forming a medical implant, includes creating an opening in an elongate member such that an inner edge of the elongate member define the opening, and treating at least a portion of the inner edge of the elongate member.

In another embodiment, a method of placing an implant within a body of a patient, includes providing an elongate member having an inner edge, the inner edge defining an opening, at least a portion of the inner edge being treated, the elongate member including a first tail member coupled to and extending from a first end portion of the elongate member and a second tail member coupled to and extending from the first end portion of the elongate member; coupling the first tail member to bodily tissue proximate a vagina of the patient; coupling the second tail member to bodily tissue proximate the vagina of the patient; and coupling a second end portion of the elongate member to bodily tissue proximate a sacrum of the patient.

BRIEF DESCRIPTION OF THE FIGURES

The invention and the following detailed description of certain embodiments, thereof, may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

In general, the invention is directed to systems, methods, and devices for treating vaginal prolapse. However, the invention may be equally employed for other treatment purposes such as pelvic organ prolapse or other pelvic disorders such as incontinence. As described below in various illustrative embodiments, the invention provides systems, methods, and devices employing a medical device configured to deliver or place an implant within a patient's body to support pelvic organs.

The term patient may be used hereafter for a person who benefits from the medical device or the methods disclosed in the present invention. For example, the patient may be a person whose body is operated with the use of the medical device disclosed by the present invention in a surgical treatment. For example, in some embodiments, the patient may be a human female, human male or any other mammal.

Figure 1:
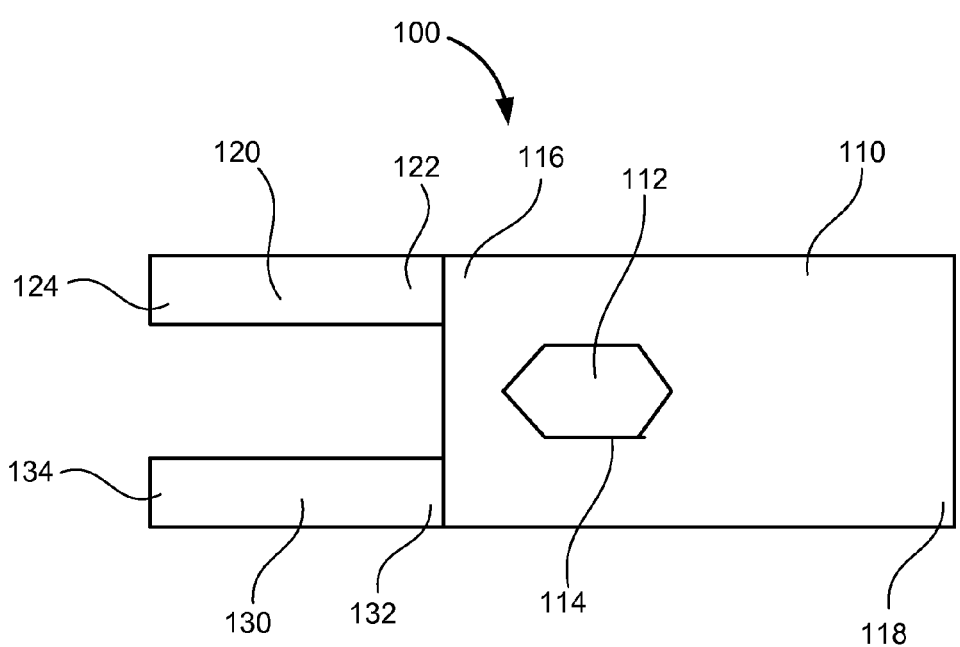
FIG. 1 is a schematic diagram of a medical device or implant according to an embodiment of the invention.

FIG. 1 is a schematic diagram of a medical device or an implant 100. The implant 100 includes an elongate member 110, a first tail member 120, and a second tail member 130. In some embodiments, the implant 100 can be used to suspend various bodily portions within a body of a patient. For example, in some embodiments, the implant 100 can be used to suspend a pelvic organ of a patient's body. In some embodiments, the medical device or implant 100 may be used to support a vagina of a patient. In some embodiments, the implant 100 can be configured to be delivered or placed within the body of the patient using a transabdominal approach or method. In other embodiments, the implant 100 can be configured to be delivered or placed within the body of the patient using a transvaginal approach or method. In yet other embodiments, the implant 100 can be delivered or placed within the body of the patient via another method.

In the illustrated embodiment, the elongate member 110 of the implant 100 defines an opening 112. Specifically, an inner edge 114 of the elongate member 110 defines or forms the perimeter of the opening 112. In some embodiments, the inner edge 114 of the elongate member 110 or a portion of the inner edge 114 has been treated or otherwise includes a treatment. In some embodiments, the inner edge 114 or a portion of the inner edge 114 has been treated or otherwise includes a treatment to provide or help provide strength to the inner edge 114 of the elongate member 110. For example, in some embodiments, the treatment may provide radial strength to the elongate member 110. In some embodiments, the treatment may help prevent the inner edge 114 of the elongate member 110 from fraying, splitting, or tearing.

In some embodiments, the treatment applied to the inner edge 114 of the elongate member 110 includes a composition change of at least a portion of the inner edge 114 of the elongate member 110. For example, the inner edge 114 may be heated, melted, or cauterized using a laser or any other heating source. The heating, melting, or cauterizing of the inner edge 114 may cause a portion of the inner edge 114 to change and have a different strength characteristic from the remainder of the elongate member or from an untreated inner edge. In some embodiments, the heating, melting, or cauterizing of the inner edge 114 may help prevent tearing or ripping of the elongate member 110 at or near the inner edge 114 when a force or pressure is placed on the elongate member 110 (for example, when the implant 100 is disposed within the body of a patient and used to support a portion of the body of the patient).

In other embodiments, the treatment applied to the inner edge 114 of the elongate member 110 includes an additive applied to the inner edge 114 of the elongate member 110. For example, in some embodiments, an adhesive or other type of strengthening coating or material may be applied to the inner edge 114 of the elongate member. The adhesive or other type of strengthening coating may cause a portion of the inner edge 114 to have a different strength characteristic from the remainder of the elongate member or from an untreated inner edge. In some embodiments, the application of an adhesive or other type of strengthening coating to the inner edge 114 may help prevent tearing or ripping of the elongate member 110 at or near the inner edge 114 when a force or pressure is placed on the elongate member 110 (for example, when the implant 100 is disposed within the body of a patient and used to support a portion of the body of the patient). In some embodiments, the additive is a stitching such as a reinforcing stitching. In other embodiments, the additive is a piece of material or fabric that is coupled to the inner edge 114 of the elongate member 110.

In some embodiments, the elongate member 110 has a tubular structure. Specifically, in some embodiments, the elongate member defines a lumen. The elongate member 110 or the lumen defined by the elongate member 110 may be of any cross sectional shape, such as a circle or a flattened oval shape.

In some embodiments, the elongate member 110 is formed of a mesh material. The mesh material may be a woven or knitted mesh material. In some embodiments, the elongate member 110 may be formed as a tubular structure such that the elongate member 110 defines a lumen. In other words, the tubular structure may be devoid of a seam.

In other embodiments, the mesh material may be formed as a planar or substantially planar sheet and may be placed in a tubular form by coupling one side of the mesh material to another side of the mesh material. The sides or edges of the mesh material may be coupled together via stitching, a heat seal, an ultrasonic weld, or any other coupling mechanism. Sides or edges of mesh materials may be rough or have projecting fibers. In some embodiments, the sides or edges of the mesh material of the elongate member 110 may be coupled together such that the rough portions of the sides or edges are not exposed (or on the outer surface of the elongate member 110). In such embodiments, the elongate member 110 may provide increased comfort to the patient as the bodily tissues of the patient may not be exposed to of the sides or edges of the mesh of the elongate member 110. For example, in some embodiments, without the rough surfaces of the edges being exposed, the elongate member 110 is prevented from (or is less likely to) damaging bodily tissue or organs that contact the elongate member 110. Additionally, such coupling or suturing may also provide radial strength to the elongate member 110.

In other embodiments, the elongate member 110 is formed of any other biocompatible material, such as a biocompatible synthetic material or a natural material.

The medical device or implant 100 includes a first tail member 120 and a second tail member 130. The tail members 120 and 130 extend from a first end portion 116 of the elongate member 110. The first end portion 116 of the elongate member 110 is disposed opposite the second end portion 118 of the elongate member 110. In some embodiments, the first tail member 120 is stitched to the first end portion 116 (or coupled to the first end portion 116 via a suture). In other embodiments, the first tail member 120 is coupled to the first end portion 116 via another coupling mechanism, such as an adhesive or a coupler. In the illustrated embodiment, end portion 122 of the first tail member 120 is coupled to the first end portion 116 of the elongate member 110.

In some embodiments, the second tail member 130 is stitched to the first end portion 116. In other embodiments, the second tail member 130 is coupled to the first end portion 116 via another coupling mechanism, such as an adhesive or a coupler. In the illustrated embodiment, end portion 132 of the second tail member 130 is coupled to the first end portion 116 of the elongate member 110.

In other embodiments, the first tail member 120 and the second tail member 130 are integral with the elongate member 110. For example, in some embodiments, the first tail member 120 and the second tail member 130 are integrally knit with the elongate member 110. The knits, weave patterns, or braid patterns of the first and second tail members 120 and 130 may be different than the knit, weave pattern, or braid pattern of the elongate member 110.

The first tail member 120 and the second tail member 130 may be formed of any biocompatible material. In some embodiments, the first tail member 120 and the second tail member 130 may be formed of a mesh material. The mesh material may be knitted or woven material.

In some embodiments, the elongate member 110 behaves differently (or has different properties) in the body of the patient than the first tail portion 120 and the second tail portion 130. In some embodiments, the elongate member 110 is stiffer or less flexible than the first tail member 120 and the second tail member 130. In such embodiments, the first tail member 120 and the second tail member 130 are more flexible or more compliant than the elongate member 110. In some embodiments, first tail member 120 may be more or less flexible than the second tail member 130. As the first tail member 120 and the second tail member 130 are flexible, in some embodiments, they may be configured to assume the flexibility or elasticity of the portions of the body to which they are attached. For example, the first tail member 120 and the second tail member 130 may be configured to have or assume the flexibility or elasticity of the vaginal walls to which they are attached. As the elongate member 110 is more stiff (less flexible), in some embodiments, the elongate member 110 is configured to provide support to the body portions of the patient without flexing or stretching (or without a substantial amount of flexing or stretching).

In some embodiments, the medical implant or medical device 100 is configured to be placed within a body of a patient and configured to provide support to a portion of the body of the patient, such as a vagina of the patient. In some embodiments, the medical device 100 is configured to be placed or implanted within a body of a patient via an abdominal incision. In other embodiments, the medical implant 100 may be placed or implanted within the body of the patient via another incision or opening such as a vaginal incision.

In some embodiments, the elongate member 110 is configured to be attached to a sacrum of a patient or to a location proximate the sacrum of the patient. For example, the end portion 118 of the elongate member 110 may be configured to be coupled or attached to the sacrum of the patient. The end portion 118 may be coupled or attached to the sacrum via any type of coupling methods, such as via a suture, an anchor, or an adhesive. Alternatively, the end portion 118 of the elongate member 110 may be passed through the coupling tissue to anchor or couple the medical implant 100 to or near the sacrum of the patient. In other embodiments, the elongate member 110 is configured to be coupled or attached to another anchoring portion within the body of the patient.

In some embodiments, the first tail member 120 may be coupled or attached to an anterior vaginal wall of the patient. For example, the end portion 124 of the first tail member 120 may be sutured or coupled via another coupling mechanism, such as an anchor or an adhesive, to the anterior vaginal wall of the patient. In some embodiments, the second tail member 130 may be coupled or attached to a posterior vaginal wall of the patient. For example, the end portion 134 of the second tail member 130 may be sutured or coupled via another coupling mechanism, such as an anchor or an adhesive, to the posterior vaginal wall. In other embodiments, the first tail member 102 and the second tail member 130 may be coupled to other portions of the body of the patient.

In some embodiments, a medical practitioner may modify or customize the device 100 prior to implantation into the body of the patient. For example, a medical practitioner may modify or customize the device 100 to best fit or to best serve the specific anatomy of the patient. In one embodiment, the elongate member 110 of the device 100 may be cut along a line parallel to a longitudinal axis of the elongate member 110. The medical practitioner may cut the device 100 to effectively shorten the length of the elongate member 110 (or in other words, to shorten the lumen defined by the elongate member 110). The cut may be made towards or to the opening 112. As discussed above, the treatment of the inner edge 114 helps strengthen the elongate member 110 after such cut. In some embodiments, the medical practitioner may cut the elongate member 110 in half or such that two separate pieces are formed.

Figure 2:
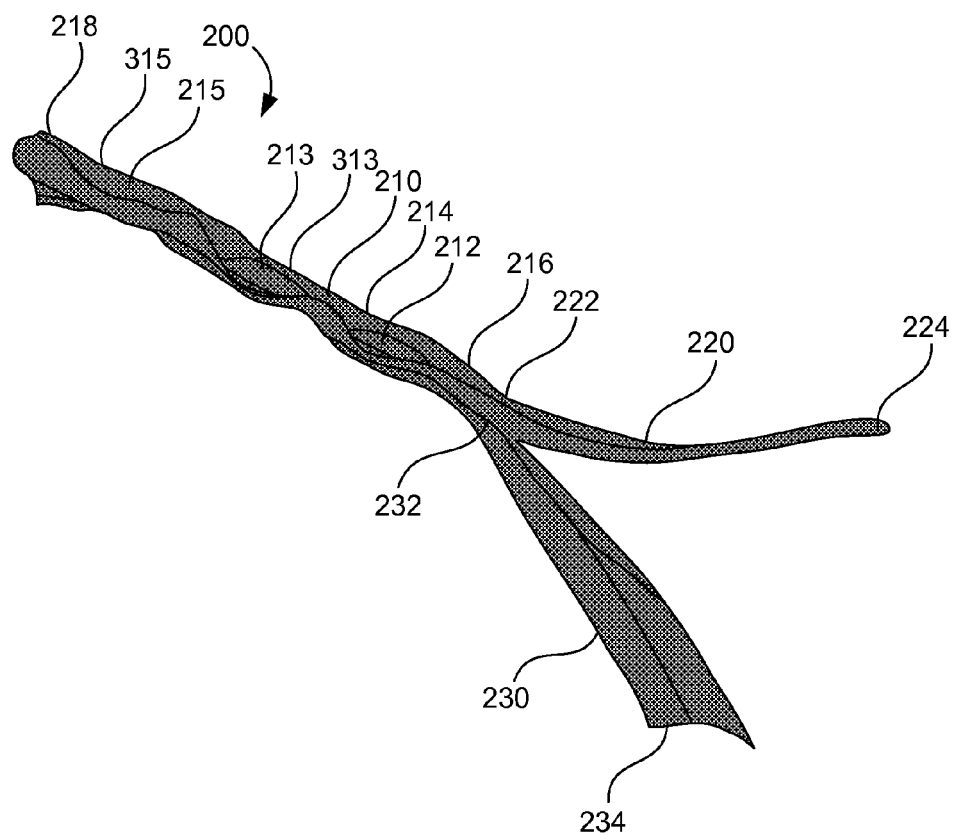
FIG. 2 is a perspective view of a medical device or implant according to an embodiment of the invention.
Figure 3:
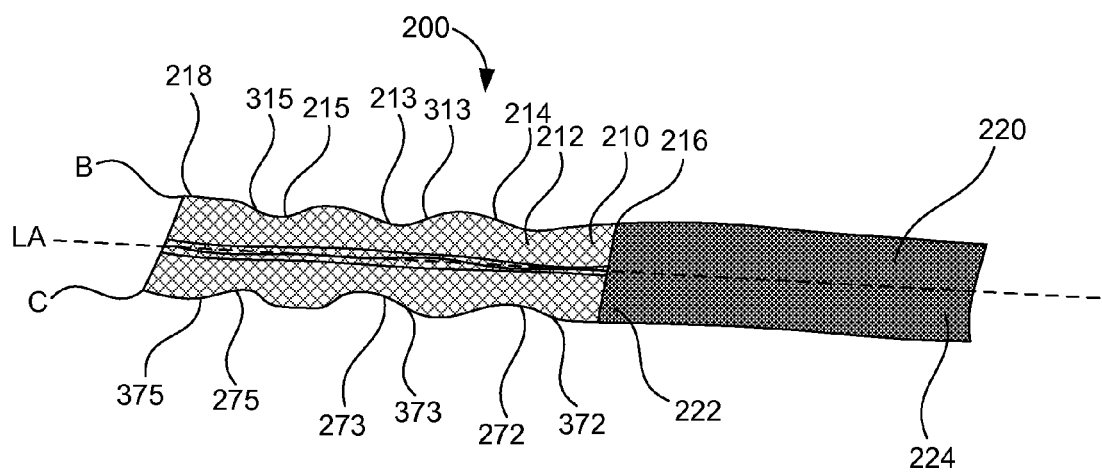
FIG. 3 is a top view of the medical device or implant of FIG. 2.
Figure 4:
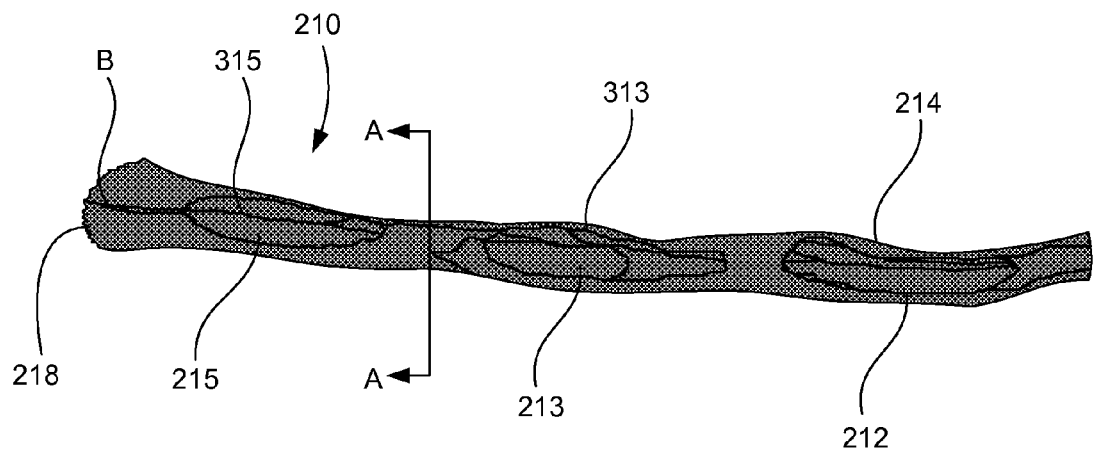
FIG. 4 is a side view of an elongate member of the medical device or implant of FIG. 2.
Figure 5:
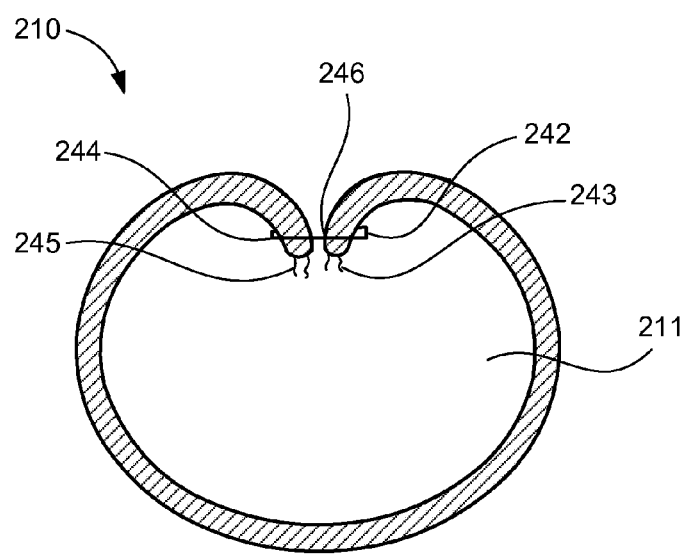
FIG. 5 is a cross-sectional view of the elongate member of FIG. 4 taken along line A-A of FIG. 4.

FIGS. 2-5 illustrate a medical device or implant 200 according to an embodiment of the invention. FIG. 2 is a perspective view of a medical device or implant 200. FIG. 3 is a top view of the medical device or implant 200. FIG. 4 is a side view of an elongate member 210 of the medical device or implant 200. FIG. 5 is a cross-sectional view of the elongate member 210 taken along line A-A of FIG. 4.

The implant 200 includes an elongate member 210, a first tail member 220, and a second tail member 230. In some embodiments, the implant 200 can be used to suspend various bodily portions within a body of a patient. For example, in some embodiments, the implant 200 can be used to suspend a pelvic organ of a patient's body. In some embodiments, the medical device or implant 200 may be used to support a vagina of a patient. In some embodiments, the implant 200 can be configured to be delivered or placed within the body of the patient using a transabdominal approach or method. In other embodiments, the implant 200 can be configured to be delivered or placed within the body of the patient using a transvaginal approach or method. In yet other embodiments, the implant 200 can be delivered or placed within the body of the patient via another method.

In the illustrated embodiment, the elongate member 210 of the implant 200 defines an opening 212. Specifically, an inner edge 214 of the elongate member 210 defines or forms the perimeter of the opening 212. In some embodiments, the inner edge 214 of the elongate member 210 or a portion of the inner edge 214 has been treated or otherwise includes a treatment. In some embodiments, the inner edge 214 or a portion of the inner edge 214 has been treated or otherwise includes a treatment to provide or help provide strength to the inner edge 214 of the elongate member 210. For example, in some embodiments, the treatment may provide radial strength to the elongate member 210. In some embodiments, the treatment may help prevent the inner edge 214 of the elongate member 210 from fraying, splitting, or tearing.

In some embodiments, the treatment applied to the inner edge 214 of the elongate member 210 includes a composition change of at least a portion of the inner edge 214 of the elongate member 210. For example, the inner edge 214 may be heated, melted, or cauterized using a laser or a heating source. The heating, melting, or cauterizing of the inner edge 214 may cause a portion of the inner edge 214 to change and have a different strength characteristic from the remainder of the elongate member 210 or from an untreated portion of the inner edge 214. In some embodiments, the heating, melting, or cauterizing of the inner edge 214 may help prevent tearing or ripping of the elongate member 210 at or near the inner edge 214 when a force or pressure is placed on the elongate member 210 (for example, when the implant 200 is disposed within the body of a patient and used to support a portion of the body of the patient). In some embodiments, the treatment (such as heating or cauterizing) causes tangs or end portions of woven mesh to bond, melt, or otherwise couple or seal together.

In other embodiments, the treatment applied to the inner edge 214 of the elongate member 210 includes an additive applied to the inner edge 214 of the elongate member 210. For example, in some embodiments, an adhesive or other type of strengthening coating or material may be applied to the inner edge 214 of the elongate member 210. Such adhesive or coating may be applied in manner. For example, the adhesive or coating may be applied to the inner edge 214 by brushing or spraying the adhesive or coating on the inner edge 214. The adhesive or other type of strengthening coating may cause a portion of the inner edge 214 to have a different strength characteristic from the remainder of the elongate member or from an untreated portion of the inner edge. In some embodiments, the application of an adhesive or other type of strengthening coating to the inner edge 214 may help prevent tearing or ripping of the elongate member 210 at or near the inner edge 214 when a force or pressure is placed on the elongate member 210 (for example, when the implant 200 is disposed within the body of a patient and used to support a portion of the body of the patient).

In other embodiments, the additive applied to the inner edge 214 may be a stitching, such as a reinforcing stitch, or a piece of material, such as a fabric or woven material, coupled to the inner edge 214.

The elongate member 210 may define any number of openings. In the illustrated embodiment, the elongate member 210 also includes or defines openings 213 and 215. The openings 213 and 215 are structurally and functionally similar to opening 212. The openings 213 and 215 are defined by the elongate member 210 (or specifically, inner edges 313 and 315 of the elongate member). Similar to inner edge 114, the inner edges 313 and 315 that define openings 213 and 215 (or at least a portion of such inner edges) can be treated or include a treatment similar to the treatment of inner edge 214. Opening 213 is disposed adjacent to opening 212 and opening 215. As best illustrated in FIGS. 2-4, opening 213 is disposed between opening 212 and 215. Additionally, in the illustrated embodiment, openings 212, 213, and 215 are disposed along a line that is substantially parallel to the longitudinal axis LA of the elongate member 210.

The elongate member 210 also includes or defines openings 272, 273, and 275. The openings 272, 273, and 275 are structurally and functionally similar to opening 212. The openings 272, 273, and 275 are defined by the elongate member 210 (or specifically, inner edges 372, 373, and 375 of the elongate member). Similar to inner edge 214, the inner edges 372, 373, and 375 that define openings 272, 273, and 275 (or at least a portion of such inner edges) can be treated or include a treatment similar to inner edge 214. As best illustrated in FIG. 3, opening 273 is disposed between opening 272 and 275. In the illustrated embodiment, openings 272, 273, and 275 are disposed along a line that is substantially parallel to the longitudinal axis L of the elongate member 210. Additionally, openings 272, 273, and 275 are disposed opposite openings 212, 213, and 215. In other words, openings 272, 273, and 275 are disposed on an opposite side of the elongate member 210 from the side on which openings 212, 213, and 215 are disposed on. For example, when viewed from an end of the elongate member 210, openings 212, 213, and 215 may be disposed at a 3 o'clock position and openings 272, 273, and 275 may be disposed at a 9 o'clock position.

In the illustrated embodiment, the elongate member 210 has a tubular structure. Specifically, the elongate member 210 has a first end portion 216 and a second end portion 218 opposite the first end portion 216 and defines a lumen 211 that extends from the first end portion 216 to the second end portion 218. The elongate member 210 or the lumen 211 defined by the elongate member 210 may be of any cross sectional shape, such as a circle or a flattened oval shape. In the illustrated embodiment, the lumen 211 extends parallel or substantially parallel to the longitudinal axis LA of the elongate member 210.

In some embodiments, the first end portion 216 and the second end portion 218 of the elongate member 210 include a treatment similar to the treatment discussed above with respect to the inner edge 214. For example, the first end portion 216 and the second end portion 218 may be heated, melted, cauterized or include a coating. The treatment may provide strength and support to the first end portion 216 and the second end portion 218 of the elongate member 210.

The elongate member 210 is formed of a mesh material. The mesh material may be a woven or knitted mesh material. In such embodiments, the openings 212, 213, 215, 272, 273, and 275 that are defined by the elongate member 210 are larger than the pours or openings of the woven or knitted mesh of the elongate member 210. In some embodiments, the mesh material includes polymeric materials such as polypropylene, polyester, polyethylene, nylon, PVC, polystyrene, and the like. An example of the mesh, out of which the elongate member 210 is formed, can be Polyform® Synthetic Mesh developed by the Boston Scientific Corporation. The Polyform® Synthetic Mesh is made from uncoated monofilament macro-porous polypropylene.

In some embodiments, the elongate member 210 may be formed as a tubular structure. In other words, the tubular structure may be devoid of a seam.

In other embodiments, the mesh material may be formed as a planar or substantially planar sheet and may be placed in a tubular form by coupling one side of the mesh material to another side of the mesh material. The sides or edges of the mesh material may be coupled together via stitching, a heat seal, an ultrasonic weld, or any other coupling mechanism. Sides or edges of mesh materials may be rough or have projecting fibers. As illustrated in FIG. 5, in the illustrated embodiment, the sides or edges 242 and 244 of the mesh material of the elongate member 210 may be coupled together via a suture 246 such that the rough portions 243 and 245 of the sides or edges 242 and 244 are not exposed (or on the outer surface of the elongate member 210). In such embodiments, the elongate member 210 may provide increased comfort to the patient as the bodily tissues of the patient may not be exposed to of the sides or edges of the mesh of the elongate member 210. For example, in some embodiments, without the rough surfaces of the edges being exposed, the elongate member 210 is prevented from (or is less likely to) damaging bodily tissue or organs that contact the elongate member 210. Additionally, such coupling or suturing may also provide radial strength to the elongate member 210.

In some embodiments, the coupling of the sides or edges 242 and 244 occurs at an orientation as illustrated in FIG. 5. For example, in the illustrated embodiment the coupling occurs at the 12 o'clock position. Also in the illustrated embodiment, the openings defined by the elongate member 210 are disposed at the 3 o'clock and the 9 o'clock positions. In other words, the coupling or suturing of the ends is disposed between the rows of openings.

In other embodiments, the elongate member 210 is formed of any other biocompatible material, such as a biocompatible synthetic material or a natural material. In such embodiments, the materials are not necessarily woven or knitted.

The medical device or implant 200 includes a first tail member 220 and a second tail member 230. The tail members 220 and 230 extend from the first end portion 216 of the elongate member 210. The first end portion 216 of the elongate member 210 is disposed opposite the second end portion 218 of the elongate member 210. In some embodiments, the first tail member 220 is stitched to the first end portion 216 (or coupled to the first end portion 216 via a suture). In other embodiments, the first tail member 220 is coupled to the first end portion 216 via another coupling mechanism, such as an adhesive or a coupler. In the illustrated embodiment, end portion 222 of the first tail member 220 is coupled to the first end portion 216 of the elongate member 210.

In some embodiments, the second tail member 230 is stitched to the first end portion 216. In other embodiments, the second tail member 230 is coupled to the first end portion 216 via another coupling mechanism, such as an adhesive or a coupler. In the illustrated embodiment, end portion 232 of the second tail member 230 is coupled to the first end portion 216 of the elongate member 210.

The first tail member 220 and the second tail member 230 may be formed of any biocompatible material. In some embodiments, the first tail member 220 and the second tail member 230 may be formed of a mesh material. The mesh material may be knitted or woven material.

In some embodiments, the elongate member 210 behaves differently (or has different properties) in the body of the patient than the first tail portion 220 and the second tail portion 230. In some embodiments, the elongate member 210 is stiffer or less flexible than the first tail member 220 and the second tail member 230. In such embodiments, the first tail member 220 and the second tail member 230 are more flexible or more compliant than the elongate member 210. For example, in some embodiments, the first tail member 220 and the second tail member 230 may be formed of a material that is more flexible than the material that forms the elongate member 210. In other embodiments, the first tail member 220 and the second tail member 230 may have a different knit or weave pattern than the elongate member 210.

In some embodiments, first tail member 220 may be more or less flexible than the second tail member 230. In other embodiments, the first tail member 220 and the second tail member 230 may have the same flexibility.

In some embodiments, the materials or the properties of the different materials that form the device provide for the different flexibilities of the different portions or members of the device. For example, different weave or knit patterns of the different portions or members of the device may provide the different flexibilities. Some portions of the device may include reinforcements or reinforcing members. In some embodiments, the filaments that form the device may have varying thicknesses or cross-sectional sizes to provide for the different flexibilities.

As the first tail member 220 and the second tail member 230 are flexible, in some embodiments, they may be configured to assume the flexibility or elasticity of the portions of the body to which they are attached. For example, the first tail member 220 and the second tail member 230 may be configured to have or assume the flexibility or elasticity of the vaginal walls to which they are attached. As the elongate member 210 is more stiff (less flexible), in some embodiments, the elongate member 210 is configured to provide support to the body portions of the patient without flexing or stretching (or without a substantial amount of flexing or stretching).

In some embodiments, the medical implant or medical device 200 is configured to be placed within a body of a patient and configured to provide support to a portion of the body of the patient, such as a vagina of the patient. In some embodiments, the medical device 200 is configured to be placed or implanted within a body of a patient via an abdominal incision. In other embodiments, the medical implant 200 may be placed or implanted within the body of the patient via another incision or opening such as a vaginal incision.

In some embodiments, the elongate member 210 is configured to be attached to a sacrum of a patient or to a location proximate the sacrum of the patient. For example, the end portion 218 of the elongate member 210 may be configured to be coupled or attached to the sacrum of the patient. The end portion 218 may be coupled or attached to the sacrum via any type of coupling methods, such as via a suture, an anchor, or an adhesive. Alternatively, the end portion 218 of the elongate member 210 may be passed through the coupling tissue to anchor or couple the medical implant 200 to or near the sacrum of the patient. In other embodiments, the elongate member 210 is configured to be coupled or attached to another anchoring portion within the body of the patient.

In some embodiments, the first tail member 220 may be coupled or attached to an anterior vaginal wall of the patient. For example, the end portion 224 of the first tail member 220 may be sutured or coupled via another coupling mechanism, such as an anchor or an adhesive, to the anterior vaginal wall of the patient. In some embodiments, the second tail member 230 may be coupled or attached to a posterior vaginal wall of the patient. For example, the end portion 234 of the second tail member 230 may be sutured or coupled via another coupling mechanism, such as an anchor or an adhesive, to the posterior vaginal wall. In other embodiments, the first tail member 202 and the second tail member 230 may be coupled to other portions of the body of the patient.

In some embodiments, a medical practitioner may modify or customize the device 200 prior to implantation or placement into the body of the patient. For example, a medical practitioner may modify or customize the device 200 to best fit or to best serve the specific anatomy of the patient. In one embodiment, the elongate member 210 of the device 200 may be cut along a line parallel to a longitudinal axis of the elongate member 110 (such as along lines B and C). The medical practitioner may cut the device 200 to effectively shorten the length of the elongate member 210 (or in other words, to shorten the lumen defined by the elongate member 210) and effectively lengthen the length of the tail members 220 and 230. The cut or cuts may be made towards or to one of the openings (such as the opening 112). The openings may provide a guide to the medical practitioner and may also allow or help the medical practitioner appropriately size the implant 200. As discussed above, the treatment of the inner edge 214 (and the other inner edges) helps strengthen the elongate member 210 after such cut or cuts. In some embodiments, the medical practitioner may cut the elongate member 210 in half or such that two separate pieces are formed.

Figure 6:
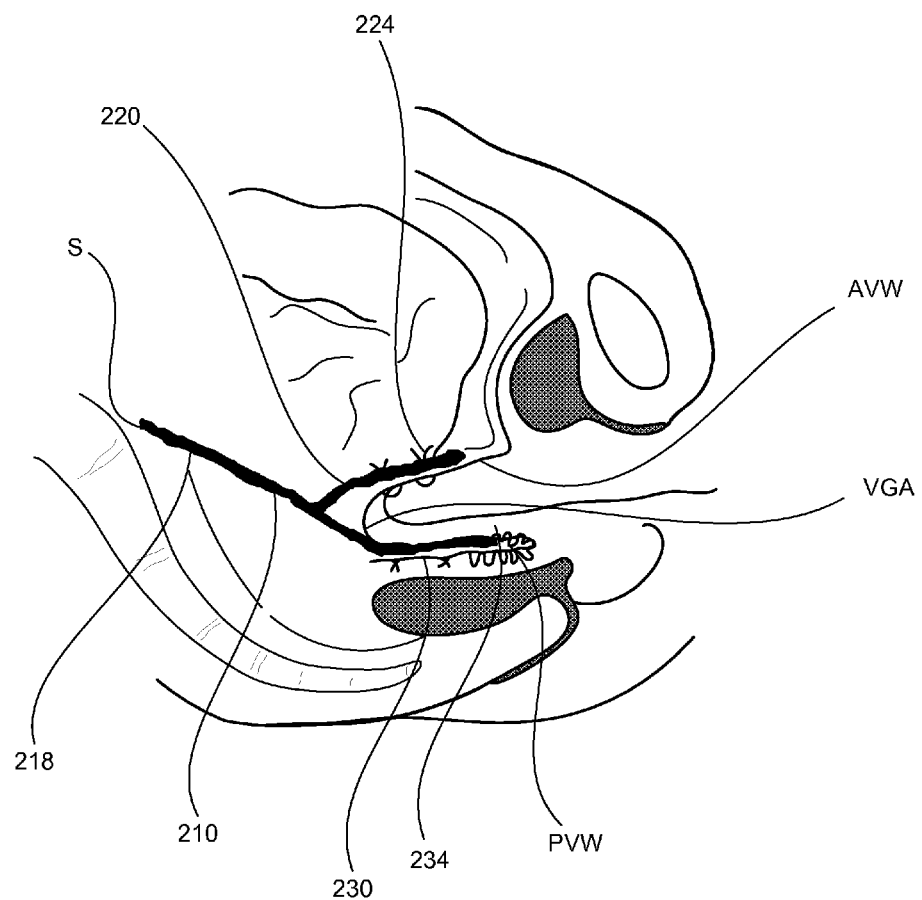
FIG. 6 is a schematic diagram of the medical device or implant of FIG. 2 disposed within a body of a patient.

FIG. 6 schematically illustrates the medical device or implant 200 disposed within a body of a patient. End portion 224 of the first tail member 220 is coupled or attached to an anterior vaginal wall AVW of the patient. End portion 234 of the second tail member 230 is coupled or attached to a posterior vaginal wall PVW of the patient. End portion 218 of the elongate member 210 is coupled or attached to the sacrum or tissue proximate the sacrum of the patient. As illustrated, the implant 200 may surround or cup the vaginal apex VGA of the patient. Accordingly, the implant 200 may provide support to the vagina and the vaginal apex VGA of the patient. Additionally, the device 200 may be disposed within the body of the patient such that an end portion of the device 200 is in contact with or disposed adjacent the vaginal apex VGA of the patient.

Figure 7:
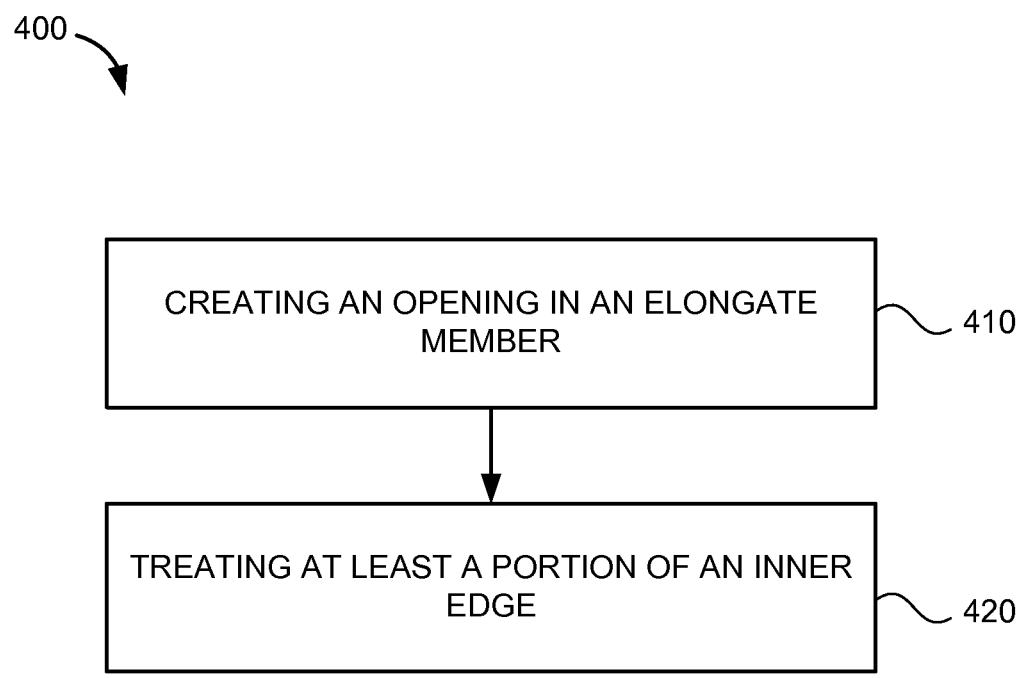
FIG. 7 is a flow chart of a process of making a medical device or implant.

FIG. 7 is a flow chart for a method of making, forming, or manufacturing a medical device or implant 400 according to an embodiment of the invention. The method includes at 410 creating an opening in an elongate member such that an inner edge of the elongate member defines the opening. In some embodiments, the opening is created by cutting a portion of the elongate member with a cutting device, such as a knife, a blade, or scissors. In other embodiments, the opening is created using a different method or different tool. In some embodiments, the elongate member is formed of a mesh material. In such embodiments, the opening created in the elongate member is larger than the pours or openings of the mesh. For example, in some embodiments, the opening created in the elongate member is 5 times or 10 times or more than 15 times the size of the pours of the mesh material.

The method 400 also includes treating at least a portion of the inner edge that defines the opening. In some embodiments, the treatment is configured to change at least a portion of the inner edge to strengthen the inner edge to help prevent ripping or tearing of the inner edge. For example, the inner edge may be heated or cauterized using a laser or other heating device or heat source to melt or otherwise treat at least a portion of the inner edge of the elongate member. In other embodiments, a coating is applied to the inner edge to treat the inner edge. The coating may be an adhesive or other coating that is configured to couple to the inner edge of the elongate member and provide strength to the inner edge. In some embodiments, the coating may be applied with a tool such as a brush or sprayed on to the inner edge. In other embodiments, another method may be used to coat the inner edge.

The cutting of the elongate member may be performed by either a manufacture of the device or a medical practitioner or user of the device. Similarly, the treating of the edge portion may also be performed by either a manufacture of the device or a medical practitioner or user of the device.

In some embodiments, the method includes forming the elongate member. In some embodiments, the forming of the elongate member includes forming a tubular member. In some embodiments, the tubular member may be formed by coupling edges of a planer sheet or material together. The coupling may be done via stitching, couplers, an adhesive, or any other method. In some embodiments, the tubular member may be inverted or otherwise turned inside out such that the seam is disposed on the inside of the lumen defined by the lumen defined by the tubular elongate member. In some embodiments, the tubular member may be inverted by passing one end portion of the tubular member through the lumen defined by the tubular member until it passes entirely through the lumen.

In some embodiments, the elongate member is formed of a mesh material. In some embodiments, the method includes knitting or weaving the material of the elongate member.

In some embodiments, the method includes coupling tail members to the elongate member. In one embodiment, the method includes coupling a first tail member to a first end portion of the elongate member and coupling a second tail member to the first end portion of the elongate member. In some embodiments, the tail members are coupled to the elongate member via sutures, couplers, or an adhesive. In other embodiments, the tail members are coupled to the elongate member using another coupling method.

Figure 8:
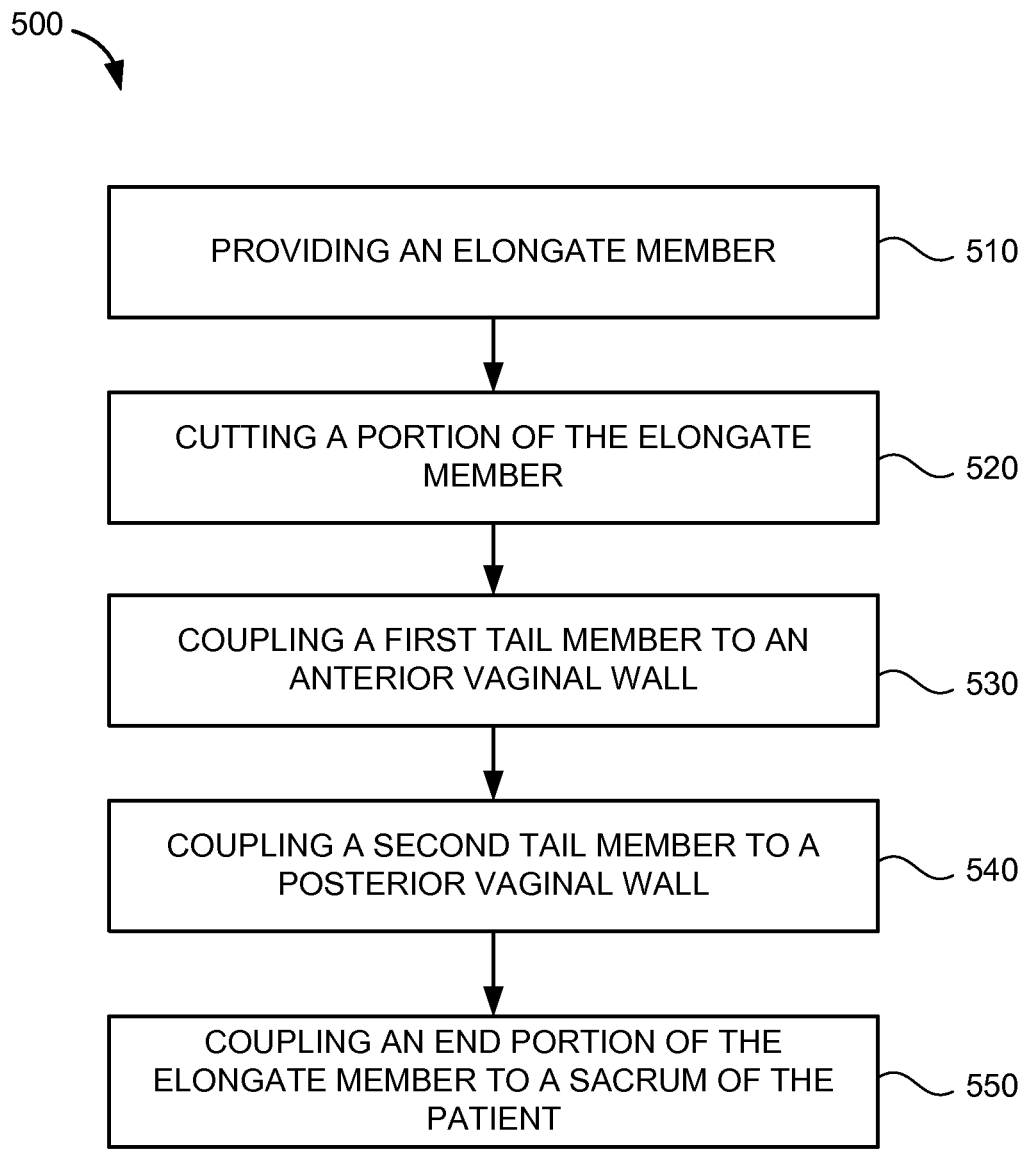
FIG. 8 is a flow chart of a process of placing a medical device or implant within a body of a patient.

FIG. 8 is a flow chart for a method of placing or implanting an implant within a body of a patient 500 according to an embodiment of the invention. The method 500 includes at 510 providing an elongate member having an inner edge, the inner edge defining an opening, at least a portion of the inner edge being treated, the elongate member including a first tail member coupled to and extending from a first end portion of the elongate member and a second tail member coupled to and extending from the first end portion of the elongate member; at 520 cutting a portion of the elongate member; at 530 coupling the first tail member to bodily tissue proximate a vagina of the patient; at 540 coupling the second tail member to bodily tissue proximate the vagina of the patient; and at 550 coupling a second end portion of the elongate member to bodily tissue proximate a sacrum of the patient.

In some embodiments, at 520 the cutting of the elongate member includes cutting from an outside edge of the elongate member to or towards the opening of the elongate member. In some embodiments, the cutting includes cutting from the opening of the elongate member to another opening of the elongate member. In some embodiments, the elongate member is cut based on the size or bodily dimensions of the patient. In some embodiments, the implant is cut in two pieces such that both pieces may be placed within the body of the patient.

In some embodiments, a method 500 for placing an implant in a body of a patient, the method includes inserting the implant inside the body; attaching a portion of the implant to an anterior vaginal wall, wherein the portion attaching to the anterior vaginal wall; attaching a portion of the implant to a posterior vaginal wall.

In some embodiments, the method includes creating an abdominal incision for delivering the implant inside the body laparoscopically. In some embodiments, the elongate member includes a portion configured to be attached proximate a sacrum, the method further comprising attaching the elongate member to the sacrum or to tissue proximate the sacrum.

In some embodiments, the attaching of the portions of the implant to bodily tissue includes suturing the portions of the implant to bodily tissue with a suture, an anchor, or with an adhesive. In other embodiments, other coupling methods may be used.

In some embodiments, the method includes closing the abdominal incision and other incisions.

In some embodiments, an implant includes an elongate member having an inner edge, the inner edge defining an opening, at least a portion of the inner edge being treated. In some embodiments, the elongate member is a tubular member. In some embodiments, the elongate member defines a lumen, the opening being in fluid communication with the lumen. In some embodiments, the elongate member is formed of a mesh material.

In some embodiments, the implant includes a first tail member coupled to and extending from a first end portion of the elongate member and a second tail member coupled to and extending from the first end portion of the elongate member. In some embodiments, at least a portion of the inner edge being treated via a cauterization process. In some embodiments, at least a portion of the inner edge being treated via a melting process.

In some embodiments, the inner edge is a first inner edge, the opening being a first opening, the elongate member having a second inner edge, the second inner edge defining a second opening, at least a portion of the second inner edge being treated. In some embodiments, the inner edge is a first inner edge, the opening being a first opening, the elongate member having a second inner edge, the second inner edge defining a second opening, at least a portion of the second inner edge being treated, the second opening being disposed adjacent the first opening. In some embodiments, the inner edge is a first inner edge, the opening being a first opening, the elongate member having a second inner edge, the second inner edge defining a second opening, at least a portion of the second inner edge being treated, the first opening being disposed on a first side of the elongate member, the second opening being disposed on a second side of the elongate member, the first side of the elongate member being opposite the second side of the elongate member.

In some embodiments, a method of forming a medical implant includes creating an opening in an elongate member such that an inner edge of the elongate member define the opening and treating at least a portion of the inner edge of the elongate member. In some embodiments, the treating the at least a portion of the inner edge of the elongate member includes cauterizing the at least a portion of the inner edge. In some embodiments, the treating the at least a portion of the inner edge of the elongate member includes cauterizing the at least a portion of the inner edge using a heat source. In some embodiments, the treating the at least a portion of the inner edge of the elongate member includes cauterizing the at least a portion of the inner edge using a laser.

In some embodiments, the method includes forming the elongate member, the elongate member defining a lumen. In some embodiments, the method includes forming the elongate member by coupling a first edge of a planar substrate with a second edge of a planar substrate. In some embodiments, the method includes forming the elongate member by coupling a first edge of a planar substrate with a second edge of a planar substrate and inverting the elongate member. In some embodiments, the method includes coupling a first tail member to a first end portion of the elongate member and coupling a second tail member to the first end portion of the elongate member.

In some embodiments method of placing an implant within a body of a patient includes providing an elongate member having an inner edge, the inner edge defining an opening, at least a portion of the inner edge being treated, the elongate member including a first tail member coupled to and extending from a first end portion of the elongate member and a second tail member coupled to and extending from the first end portion of the elongate member; coupling the first tail member to bodily tissue proximate a vagina of the patient; coupling the second tail member to bodily tissue proximate the vagina of the patient; and coupling a second end portion of the elongate member to bodily tissue proximate a sacrum of the patient.

In some embodiments, the method of claim includes cutting a portion of the elongate member.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. An implant, comprising:
    an elongate member having a first longitudinal side and a second longitudinal side opposite to the first longitudinal side, the elongate member having a first end portion and a second end portion, the first longitudinal side defining a first edge portion having a first opening, the second longitudinal side defining a second edge portion having a second opening, the first longitudinal side being coupled to the second longitudinal side to form a lumen extending between the first end portion and the second end portion, the first edge portion and the second edge portion being treated;
    a first tail member coupled to and extending from the first end portion of the elongate member; and
    a second tail member coupled to and extending from the first end portion of the elongate member,
    wherein each of the elongate member, the first tail member, and the second tail member includes a mesh material.

2. The implant of claim 1, wherein the elongate member is a tubular member.

3. The implant of claim 1, wherein the first edge portion and the second edge portion have a composition different than a remainder of the elongate member, the remainder of the elongate member being untreated.

4. The implant of claim 1, wherein the first edge portion and the second edge portion have a strength characteristic different from a remainder of the elongate member.

5. The implant of claim 1, wherein the first edge portion and the second edge portion include a strengthening coating.

6. The implant of claim 1, wherein the first edge portion and the second edge portion are treated via a cauterization process.

7. The implant of claim 1, wherein the first edge portion and the second edge portion are treated via a melting process.

8. The implant of claim 1, wherein the first opening is disposed a first distance along the first longitudinal side from the second end portion of the elongate member, and the second opening is disposed a second distance along the second longitudinal side from the second end portion of the elongate member, the second distance being the same as the first distance.

9. The implant of claim 1, further comprising:
    a suture that couples the first longitudinal side with the second longitudinal side.

10. The implant of claim 1, wherein the first longitudinal side defines a third edge portion having a third opening, and the second longitudinal side defines a fourth edge portion having a fourth opening, wherein the third edge portion and the fourth edge portion are treated.

11. A method of forming a medical implant, comprising:
    creating a first opening and a second opening in an elongate member, the elongate member having a first longitudinal side and a second longitudinal side opposite to the first longitudinal side, the elongate member having a first end portion and a second end portion, the first longitudinal side defining a first edge portion having the first opening, the second longitudinal side defining a second edge portion having the second opening;
    treating the first edge portion and the second edge portion of the elongate member;

coupling the first longitudinal side to the second longitudinal side to form a lumen extending between the first end portion of the elongate member and the second end portion of the elongate member;

coupling a first tail member to the first end portion of the elongate member; and coupling a second tail member to the first end portion of the elongate member, wherein each of the elongate member, the first tail member, and the second tail member includes a mesh material.

12. The method of claim 11, wherein the treating the first edge portion and the second edge portion of the elongate member includes cauterizing the first edge portion and the second edge portion.

13. The method of claim 11, wherein the treating the first edge portion and the second edge portion of the elongate member includes cauterizing the first edge portion and the second edge portion using a heat source.

14. The method of claim 11, wherein the treating the first edge portion and the second edge portion of the elongate member includes cauterizing the first edge portion and the second edge portion using a laser.

15. The method of claim 11, wherein the coupling the first longitudinal side to the second longitudinal side include coupling the first longitudinal side to the second longitudinal side with a suture to form a seam.

16. The method of claim 15, further comprising:

inverting the elongate member including turning the elongate member inside out such that the seam is disposed inside the lumen.

17. The method of claim 11, wherein the elongate member is less flexible than the first tail member and the second tail member.

18. A method of placing an implant within a body of a patient, comprising:

providing an implant having an elongate member, the elongate member having a first longitudinal side and a second longitudinal side opposite to the first longitudinal side, the elongate member having a first end portion and a second end portion, the first longitudinal side defining a first edge portion having a first opening, the second longitudinal side defining a second edge portion having a second opening, the first longitudinal side being coupled to the second longitudinal side to form a lumen extending between the first end portion and the second end portion, the first edge portion and the second edge portion being treated, the implant including a first tail member coupled to and extending from the first end portion of the elongate member and a second tail member coupled to and extending from the first end portion of the elongate member, wherein each of the elongate member, the first tail member, and the second tail member includes a mesh material;

coupling the first tail member to bodily tissue proximate a vagina of the patient;

coupling the second tail member to bodily tissue proximate the vagina of the patient; and coupling a second end portion of the elongate member to bodily tissue proximate a sacrum of the patient.

19. The method of claim 18, further comprising:

cutting a portion of the elongate member.

\* \* \* \* \*